United States Patent [19]

Eckhardt et al.

[11] Patent Number: 4,966,908
[45] Date of Patent: Oct. 30, 1990

[54] ISONICOTINIC ACID AMIDES FOR PROTECTING PLANTS AGAINST DISEASE

[75] Inventors: Wolfgang Eckhardt, Lörrach, Fed. Rep. of Germany; Alfred Meyer, Basel; Walter Kunz, Oberwil, both of Switzerland

[73] Assignee: Ciba-Geigy Corporation, Ardsley, N.Y.

[21] Appl. No.: 323,456

[22] Filed: Mar. 14, 1989

[30] Foreign Application Priority Data

Mar. 21, 1988 [CH] Switzerland ............... 1068/88

[51] Int. Cl.$^5$ .................. A01N 43/40; C07D 413/12
[52] U.S. Cl. ............................ 514/340; 514/341; 514/342; 514/336; 546/275; 546/276; 546/277; 546/278; 546/279; 546/280; 546/283; 546/284
[58] Field of Search .......... 546/275, 276, 277, 278, 546/279, 280, 283, 284; 71/90, 92, 94; 514/340, 341, 342, 336

[56] References Cited

FOREIGN PATENT DOCUMENTS 1072443  2/1980  Canada .
0013360  7/1980  European Pat. Off. .
0246507  11/1987  European Pat. Off. .
384929   2/1965  Switzerland .
923387   4/1963  United Kingdom .

OTHER PUBLICATIONS

CA 110: 95009m, by Yoshida, Hiroshi.
Ozawa et al., CA 107: 193029a.
Kay, CA 98: 89160w.
Chem. Abstract, 57: 4769a (1962), Abstract of Acta Fa. Pharm. Brun. Bratislav., 4, 65, 66 (1962).

Primary Examiner—Jane T. Fan
Attorney, Agent, or Firm—Edward McC. Roberts; George R. Dohmann

[57] ABSTRACT

Novel substituted isonicotinic acid amides and isonicotinic acid hydrazides of the general formula

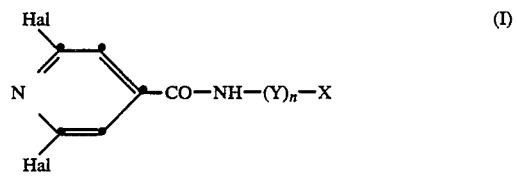

in which Hal, each independently of the other, is fluorine, chlorine, bromine or iodine, preferably fluorine, chlorine or bromine;

Y is $CH-R_1$ or NH;

n is 1 or 0;

$R_1$ is hydrogen or $C_1-C_4$alkyl;

X is a 5-membered saturated or unsaturated, unsubstituted or $C_1-C_8$alkyl-, halogen-, trifluoromethyl-, cyano- or nitro-substituted heterocycle having from 1 to 3 hereto atoms, such as N, O or S, wherein the heterocycle may, in addition, contain an oxo or thiono group.

The novel active ingredients have plant-protecting properties and are suitable especially for the preventive protection of plants against attack by phytopathogenic microorganisms such as fungi, bacteria and viruses.

9 Claims, No Drawings

ISONICOTINIC ACID AMIDES FOR PROTECTING PLANTS AGAINST DISEASE

The present invention relates to novel substituted isonicotinic acid amides and isonicotinic acid hydrazides of the following formula I. The invention relates also to the preparation of those substances and to compositions containing at least one of those compounds as active ingredient. The invention furthermore relates to the preparation of the said compositions and to the use of the active ingredients or compositions for protecting plants against attack by harmful microorganisms, for example plant-damaging fungi, bacteria and viruses.

The compounds of the invention correspond to the general formula I

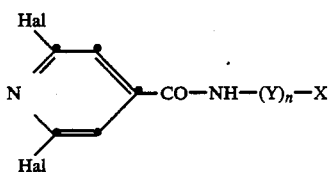

in which

Hal, each independently of the other, is fluorine, chlorine, bromine or iodine, preferably fluorine, chlorine or bromine;

Y is $CH-R_1$ or NH;

n is 1 or 0;

$R_1$ is hydrogen or $C_1-C_4$alkyl;

X is a 5-membered saturated or unsaturated, unsubstituted or $C_1-C_8$alkyl-, halogen-, trifluoromethyl-, cyano- or nitro-substituted heterocycle having from 1 to 3 hetero atoms, such as N, O or S, wherein the heterocycle may, in addition, contain an oxo or thiono group.

Alkyl on its own or as a component of another substituent is straight-chain or branched alkyl. Depending on the number of carbon atoms indicated it represents, for example, one of the following groups: methyl, ethyl and the isomers of propyl, butyl, pentyl, hexyl, heptyl or octyl, such as, for example, isopropyl, isobutyl, tert.-butyl, sec.-butyl or isopentyl. 5-membered heterocycles include, for example: furan, tetrahydrofuran, thiophene, pyrrole, imidazole, imidazoline, pyrazole, pyrazoline, triazole, oxazole, isoxazole, thiazole, isothiazole, thiadiazole, oxadiazole, thiazoline or oxazoline.

As components of compounds of formula I the heterocyclic radicals are bonded, for example, as: furan-2-yl, furan-3-yl, thiophen-2-yl, thiophen-3-yl, imidazol-2-yl, 4,5-imidazolin-2-yl, pyrazol-3-yl, pyrazolin-3-yl, 1,2,4-triazol-3-yl, 1,2,4-triazol-4-yl, oxazol-2-yl, isoxazol-5-yl, isoxazol-3-yl, thiazol-2-yl, isothiazol-3-yl, isothiazol-5-yl, 1,3,4-thiadiazol-2-yl, 1,3,4-thiadiazol-3-yl, 1,3,4-oxadiazol-3-yl or 1,2,4-oxadiazol-3-yl and also 3-thiono-1,2-dithia-4-azol-5-yl, 2-thionothiazolin-4-on-3-yl or 2-oxy-4,5-dihydrooxazol-3-yl.

Of the compounds of formula I the following groups are preferred on account of their outstanding biological activity:

1. Compounds of formula Ia

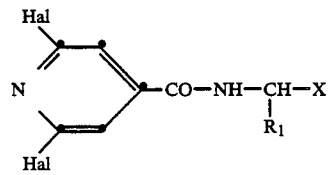

in which

Hal, each independently of the other, is fluorine, chlorine or bromine;

R: is hydrogen or $C_1-C_4$alkyl;

X is a heterocycle as specified for formula I.

2. Compounds according to claim 1 of formula Ib

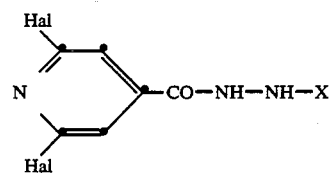

in which

Hal, each independently of the other, is fluorine, chlorine or bromine; X is a heterocycle as specified for formula I.

3. Compounds of formula Ic

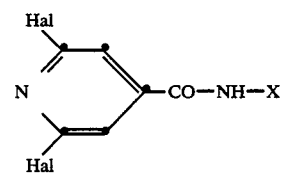

in which

Hal, each independently of the other, is fluorine, chlorine or bromine;

X is a heterocycle as specified for formula I.

Preferred active ingredients of formula I are those that have the following substituents or combinations of these substituents:

1.1 Compounds of formula Ia in which:

Hal is chlorine or bromine;

$R_1$ is hydrogen;

X is furan-2-yl, 1,2,4-triazol-3-yl, thiazol-2-yl, thiazol-5-yl, isothiazol-3-yl, oxazol-2-yl, isoxazol-3-yl, isoxazol-5-yl, 1,3,4-thiadiazol-2-yl, 1,2,4-thiadiazol-3-yl or 3-thiono-1,2-dithia-4-azol-5-yl.

1.2 Compounds of formula Ib in which:

Hal is chlorine or bromine;

X is furan-2-yl, 1,2,4-triazol-3-yl, thiazol-2-yl, thiazol-5-yl, isothiazol-3-yl, oxazol-2-yl, isoxazol-3-yl, isoxazol-5-yl, 1,3,4-thiadiazol-2-yl, 1,2,4-thiadiazol-3-yl or 3-thiono-1,2-dithia-4-azol-5-yl.

1.3 Compounds of formula Ic in which

Hal is chlorine or bromine;

X is furan-2-yl, 1,2,4-triazol-3-yl, thiazol-2-yl, thiazol-5-yl, isothiazol-3-yl, oxazol-2-yl, isoxazol-3-yl, isoxazol-5-yl, 1,3,4-thiadiazol-2-yl, 1,2,4-thiadiazol-3-yl or 3-thiono-1,2-dithia-4-azol-5-yl.

Also especially preferred are compounds of formulae Ia, Ib and Ic in which Hal is chlorine and R: and X are as defined for the said formulae.

Of the groups of compounds listed above, compounds of formula Ic are especially preferred.

The following compounds are distinguished by especially advantageous plant-protecting properties:

3-methylisoxazole-5-(2,6-dichloroisonicotinic acid) amide, 5-methylisoxazole-3-(2,6-dichloroisonicotinic acid) amide, α-methylfurfuryl-2,6-dichloroisonicotinic acid amide, 3-methylisothiazole-5-(2,6-dichloroisonicotinic acid) amide.

Some 2,6-dihaloisonicotinic acid derivatives are already known. For example, 2,6-dihaloisonicotinic acid derivatives, for example aliphatic amides, are described as herbicides in British Patent Specification No. 923 387. Furthermore, U.S patent Specification No. 4 137 067 and Canadian Patent Specification No. 1 072 443 disclose 2,6-dichloroisonicotinic acid hydrazides for controlling phytopathogenic microorganisms. In addition, 2,6-dihaloisonicotinic acid derivatives are known as tuberculostatic agents (cf. Acta Fac. Pharm. Brun. Bratislav. 4, 65–66[1962]; Chem. Abstr. Vol. 57, 1962, 4769b).

It has now surprisingly been found that the use of compounds of formula I of the invention prevents plants from being attacked by harmful microorganisms and thus guards against damage to plants caused by such attack. A characteristic of the active ingredients of the invention is that the protection of the plants can stem both from the direct action on the plant-damaging microorganisms by means of foliar application (direct action) or soil application (systemic action) and from the activation and stimulation of the plant's own defence system (immunisation). The great advantage of the compounds of formula I is that it is possible to ensure the continued health of plants treated with these substances also through their own resources, without using further microbicidal substances during the vegetation period. Consequently it is possible by using the active ingredients of the invention to avoid the adverse side effects that may occur, for example, with direct parasite control using chemical substances, for example on the one hand as a result of damage to the useful plants (phytotoxicity) and on the other hand as a result of causing the harmful microorganisms to develop a resistance; consequently growth of the useful plants is advantageously completely undisturbed.

Owing to the double action of the compounds of formula I of the invention, that is to say on the one hand the direct control of the plant pathogens and on the other hand the increase in the general capacity of plants treated with these active ingredients to defend themselves as a result of immunisation, it is possible to achieve a broadly based protection of plants against disease. The use of the active ingredients of the invention is therefore especially suitable for practical application. In addition, the systemic activity peculiar to the compounds of formula I results in the protective effect being extended also to growing parts of the treated plants.

The general plant-protecting activity of the active ingredients of the invention is effective, for example, against the phytopathogenic fungi belonging to the following classes: Fungi imperfecti (for example Botrytis, Helminthosporium, Fusarium, Septoria, Cercospora and Alternaria); Basidiomycetes (for example of the genera Hemileia, Rhizoctonia, Puccinia); Ascomycetes (for example Venturia, Podosphaera, Erysiphe, Monilinia, Uncinula).

In addition, the active ingredients can be used with particular advantage against the following harmful organisms:

fungi, such as, for example, Oomycetes (for example Plasmopara viticola, Phytophthora infestans, Peronospora tabacina, Pseudoperonospora), Fungi imperfecti (for example Colletotrichum lagenarium, Piricularia oryzae, Cercospora nicotinae), Ascomycetes (for example Venturia inaequalis); bacteria, such as, for example, Pseudomonads (Pseudomonas lachrymans, Pseudomonas tomato, Pseudomonas tabaci); Xanthomonads (for example Xanthomonas oryzae, Xanthomonas vesicatoria); Erwinia (for example Erwinia amylovora); and viruses, such as, for example, the Tobacco Mosaic Virus.

The compounds of the invention can be used to protect plants of various useful crops.

The following species of plants, for example, are suitable for the use within the scope of the invention of compounds of formula I of the invention:

cereals (wheat, barley, rye, oats, rice, sorghum and related crops), beet (sugar beet and fodder beet), pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkin, cucumber, melons); fiber plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor), or plants such as maize, tobacco, nuts, coffee, sugar cane, tea, vines, hops, bananas and natural rubber plants, as well as ornamentals (flowers, shrubs, deciduous trees and conifers). This list does not constitute a limitation.

The following plants are to be regarded as especially suitable target crops for the application of the process of the invention: cucumber, tobacco, vines, rice, pepper, potatoes, tomatoes, wheat, barley, pears and apples.

The compounds of formula I are obtained from 2,6-dihaloisonicotinic acid halides, anhydrides or azolides, preferably from 2,6-dihaloisonicotinic acid halides, or more especially from dihaloisonicotinic acid chlorides.

The compounds of formula I are prepared by reacting: an isonicotinic acid halide of formula II

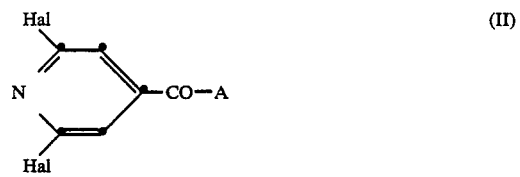

(II)

with an amine of formula III $H_2N-(Y)_n-X$     (III)

in the presence of a base in an inert solvent or without a solvent at temperatures of from −20° to 150° C., preferably from 0° to 80° C., wherein Hal is halogen, A is halogen, an acyloxy radical of the formula

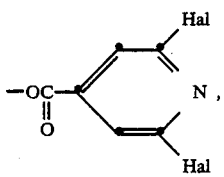

Imidazolyl or triazolyl, and X, Y and n are as defined for formula I.

Suitable bases for binding the acid in the process described above are organic and inorganic bases, for example tertiary amines, such as trialkylamines (trimethylamine, triethylamine, tripropylamine etc.), pyridine, pyridine bases (4-dimethylaminopyridine, 4-pyrrolidylaminopyridine etc.) and alcoholates, such as, for example, potassium tert.-butoxide, oxides and hydroxides, carbonates and hydrogen carbonates of alkali metals and alkaline earth metals, and also alkali metal acetates.

Suitable solvents and diluents that are inert towards the reaction are used as reaction media in the process in accordance with the respective reaction conditions. The following may be mentioned as examples:

aliphatic and aromatic hydrocarbons, such as benzene, toluene, xylenes, petroleum ether; halogenated hydrocarbons, such as chlorobenzene, methylene chloride, ethylene chloride, chloroform, carbon tetrachloride, tetrachloroethylene; ethers and ethereal compounds, such as dialkyl ethers (diethyl ether, diisopropyl ether, tert.-butyl methyl ether etc.) anisole, dioxan, tetrahydrofuran; nitriles, such as acetonitrile, propionitrile; N,N-dialkylated amides, such as dimethylformamide; dimethyl sulfoxide; ketones, such as acetone, diethyl ketone, methyl ethyl ketone; and also mixtures of such solvents with one another.

Reactions of acid chlorides and anhydrides with amines are described in Houben-Weyl, Vol. 18, page 655, and transamidation is described in Angew. Chemie 1962, page 413/412.

The preparation of the starting materials, such as acid halides and anhydrides and also heterocycles, is familiar to the person skilled in the art and known from the specialist literature [for example Houben-Weyl 5/3, p. 925; Chemistry of Heterocyclic Compounds, Arnold Weisenberger and Edward C. Taylor, Vol. 4 (1952), Vol. 6 (1953), Vol. 34 (1979), Vol. 37 (1981), Vol. 44 (1985), Vol. 45 (1986)].

The compositions that are used within the scope of the invention for protecting plants against disease and that contain the compounds of formula I as active ingredients are to be considered as part of the invention.

The compounds of formula I are normally used in the form of compositions and can be applied to the plants or locus thereof, simultaneously or in succession, with further compounds. These further compounds can be fertilisers or micronutrient donors or other preparations that influence plant growth. They can also be selective herbicides, insecticides, fungicides, bactericides, nematicides, molluscicides or mixtures of several of these preparations, if desired together with further carriers, surfactants or other application-promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

One method of applying a compound of formula I or an agrochemical composition containing at least one of these compounds is application to the plant (foliar application). The compounds of formula I can, however, also penetrate the plant through the roots via the soil (soil application), for which purpose the locus of the plant is impregnated with a liquid formulation or the compounds are applied in solid form to the soil, for example in granular form. The compounds of formula I may, however, also be applied to seeds (coating), either by impregnating the seeds with a liquid formulation of the compound, or coating them with a solid formulation (dressing). In addition, in special cases further types of application are possible, for example the selective treatment of the plant stems or buds.

The compounds of formula I are used in unmodified form or, preferably, together with the adjuvants conventionally employed in the art of formulation, and are for this purpose advantageously formulated in known manner e.g. into emulsifiable concentrates, coatable pastes, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 100 g to 600 g a.i./ha.

The formulations, i.e. the compositions, preparations or mixtures containing the compound (active ingredient) of formula I and, where appropriate, a solid or liquid adjuvant, are prepared by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Cationic surfactants are especially quatarnary ammonium salts that contain as N-substituent at least one alkyl radical having from 8 to 22 carbon atoms and as further substituents lower, unsubstituted or halogenated alkyl, benzyl or hydroxy-lower alkyl radicals.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}$–$C_{22}$), e.g. the sodium or potassium salts of oleic or stearic acid or of natural fatty acid mixtures which can be obtained e.g. from coconut oil or tallow oil.

Suitable synthetic surfactants are especially fatty alcohol sulfonates, fatty alcohol sulfates, sulfonated benzimidazole derivatives or alkylsulfonates. The fatty alcohol sulfonates or sulfates are usually in the form of alkali metal salts, alkaline earth metal salts or unsubstituted or substituted ammonium salts and contain an alkyl radical having from 8 to 22 carbon atoms.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

The compositions may also contain further auxiliaries, such as stabilisers, antifoams, viscosity regulators, binders, tackifiers as well as fertilisers or other active ingredients for achieving special effects.

The agrochemical compositions usually contain 0.1 to 99% by weight, preferably 0.1 to 95% by weight, of a compound of formula I, 99.9 to 1% by weight, preferably 99.8 to 5% by weight, of a solid or liquid adjuvant, and 0 to 25% by weight, preferably 0.1 to 25% by weight, of a surfactant.

The following Examples serve to illustrate the invention without implying any limitation.

1. Preparation Examples

Example 1.1: Preparation of 5-methylisoxazole-3-(2,6-dichloroisonicotinic acid) amide

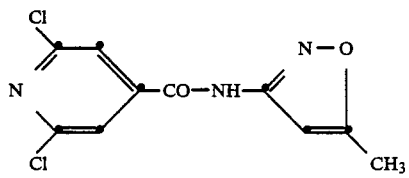

3 g (0.03 mole) of 3-amino-5-methylisoxazole and 3 g (0.03 mole) of triethylamine were dissolved in 70 ml of dichloromethane and, at from 0° to 5° C. a solution of 2,6-dichloroisonicotinic acid chloride in 30 ml of dichloromethane was added dropwise. The reacton mixture was then stirred overnight at room temperature and subsequently poured into 500 ml of water, and the product was filtered off and dried to yield 7 g (86% of the theoretical amount) of product having a melting point (decomposition) >270° C.

The compounds listed in the following are obtained in accordance with the above-described preparation.

TABLE 1

| No. | Hal | X | Physical data |
|---|---|---|---|
| 1.1 | Cl | O—N, CH₃ | m.p. 225° C. (decomp.) |
| 1.2 | Br | O—N, CH₃ | m.p. 231–232° C. |
| 1.3 | F | O—N, CH₃ | |
| 1.4 | Cl | O—N | |
| 1.5 | Br | O—N | |
| 1.6 | Cl | N—O, CH₃ | m.p. 270° C. (decomp.) |
| 1.7 | Br | N—O, CH₃ | m.p. 273–274° C. |
| 1.8 | Cl | N—S, S, S | m.p. 85° C. (decomp.) |
| 1.9 | Br | S—N, CH₃ | |
| 1.10 | Cl | N—NH, SCH₃, N | |
| 1.11 | Cl | N—N, CH₃, O | |

TABLE 1-continued

Structure: pyridine with two Hal substituents and CO—NH—X group

| No. | Hal | X | Physical data |
|---|---|---|---|
| 1.12 | Br | 3-methyl-1,2,4-oxadiazol-5-yl (N—N, CH₃, O) | |
| 1.13 | Cl | 3-methyl-1,2,4-thiadiazol-5-yl (N—N, CH₃, S) | m.p. 308–310° C. |
| 1.14 | Br | 3-methyl-1,2,4-thiadiazol-5-yl | |
| 1.15 | Cl | N-methyl substituted thiadiazole (N—N-CH₃, S) | |
| 1.16 | Br | N-methyl substituted thiadiazole (N—N-CH₃, S) | |
| 1.17 | Cl | pyrazol-type (N—NH) | m.p. 208–210° C. |
| 1.18 | Cl | CN-substituted pyrazole (N—NH, CN) | |
| 1.19 | Cl | thiazolinone (S, S, —N, =O) | m.p. 214–216° C. |
| 1.20 | Cl | 1,2,4-thiadiazol-5-yl (N—N, S) | m.p. >305° C. |
| 1.21 | Br | 1,2,4-thiadiazol-5-yl (N—N, S) | |
| 1.22 | Cl | CH₃OOC-substituted thiophene (S) | |
| 1.23 | Cl | triazole (N—NH, N) | m.p. 302–309° C. |
| 1.24 | Cl | tetrazole (—N, N, N, N) | m.p. 237–239° C. |
| 1.25 | Cl | 3-trifluoromethyl-1,2,4-thiadiazol-5-yl (N—N, CF₃, S) | m.p. 194–196° C. |
| 1.26 | Br | 3-trifluoromethyl-1,2,4-thiadiazol-5-yl (N—N, CF₃, S) | |
| 1.27 | Cl | 3-n-butyl-1,2,4-thiadiazol-5-yl (N—N, C₄H₉(n), S) | m.p. 182–184° C. |
| 1.28 | Cl | 3-tert-butyl-1,2,4-thiadiazol-5-yl (N—N, C₄H₉(tert.), S) | m.p. 232–234° C. |
| 1.29 | Cl | 3-n-octyl-1,2,4-thiadiazol-5-yl (N—N, C₈H₁₇(n), S) | |
| 1.30 | Cl | oxazolinone (—N, O, =O) | m.p. 215–218° C. |
| 1.31 | Cl | 4-methylthiazol-2-yl (N, CH₃, N, S) | m.p. 189–191° C. |
| 1.32 | Cl | 5-methylthiazol-2-yl (N, CH₃, S, N) | m.p. 112–115° C. |
| 1.33 | Cl | methylisothiazole (CH₃, N, S) | m.p. 225–228° C. |

TABLE 1-continued
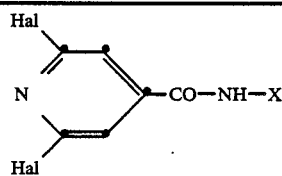
| No. | Hal | X | Physical data |
|---|---|---|---|
| 1.34 | Cl | 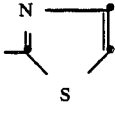 | m.p. 253–255° C. |
| 1.35 | Cl | 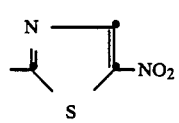 | m.p. 193–196° C. |
| 1.36 | Cl | 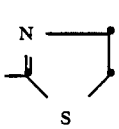 | m.p. 208–210° C. |
| 1.37 | F | 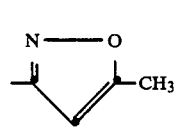 | |
| 1.38 | Br | 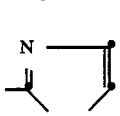 | m.p. 239–241° C. |
| 1.39 | J | 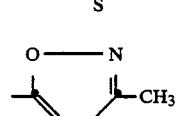 | m.p. 248–250° C. |
| 1.40 | J | 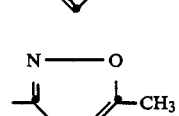 | |
TABLE 2
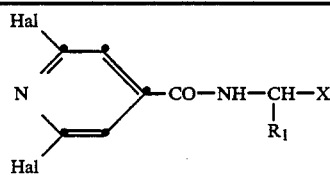
| No. | Hal | $R_1$ | X | Physical data |
|---|---|---|---|---|
| 2.1 | Cl | $CH_3$ | 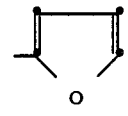 | m.p. 134–135° C. |
| 2.2 | Cl | H | 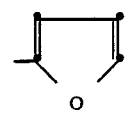 | m.p. 128–131° C. |
TABLE 2-continued
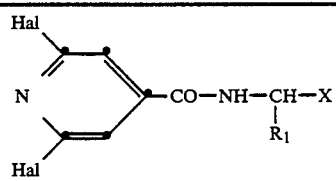
| No. | Hal | $R_1$ | X | Physical data |
|---|---|---|---|---|
| 2.3 | Cl | H | 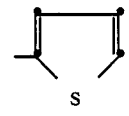 | m.p. 139–141° C. |
| 2.4 | Br | H | 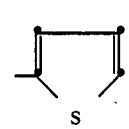 | |
| 2.5 | Br | H | 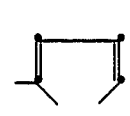 | |
| 2.6 | Br | $CH_3$ | 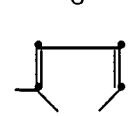 | |
TABLE 3
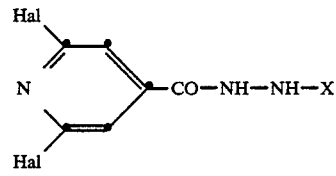
| No. | Hal | X | Physical data |
|---|---|---|---|
| 3.1 | Cl | 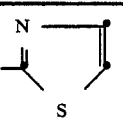 | |
| 3.2 | Br | 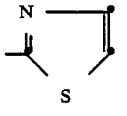 | |
| 3.3 | Cl | 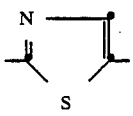 | |
| 3.4 | Cl | 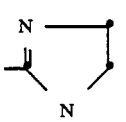 | |
| 3.5 | Cl | 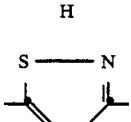 | |

TABLE 3-continued $$\text{Hal} \diagdown \text{N} \diagup \diagdown \text{CO-NH-NH-X}$$
$$\text{Hal} \diagup$$

| No. | Hal | X | Physical data |
|---|---|---|---|
| 3.6 | Br | (S—N ring with CH₃) | |
| 3.7 | Cl | (N—N—S ring with CH₃) | m.p. 229–231° C. |

Formulation Examples for active ingredients of formula I (throughout, percentages are by weight)

| 2.1. Wettable powders | a | b | c |
|---|---|---|---|
| a compound from the Tables | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7–8 moles of ethylene oxide) | — | 2% | — |
| highly dispersed silicic acid | 5% | 10% | 10% |
| kaolin | 62% | 27% | — |

The active ingredient is thoroughly mixed with the adjuvants and the mixture is homogeneously ground in a suitable mill, affording wettable powders which can be diluted with water to give suspensions of the desired concentration.

| 2.2. Emulsifiable concentrate | |
|---|---|
| a compound from the Tables | 10% |
| octylphenol polyethylene glycol ether (4–5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 2.3. Dusts | a | b |
|---|---|---|
| a compound from the Tables | 5% | 8% |
| talcum | 95% | — |
| kaolin | — | 92% |

Ready-for-use dusts are obtained by mixing the active ingredient with carriers and grinding the mixture in a suitable mill.

| 2.4. Extruder granulate | |
|---|---|
| a compound from the Tables | 10% |
| sodium lignosulfonate | 2% |

| 2.4. Extruder granulate (continued) | |
|---|---|
| carboxymethylcellulose | 1% |
| kaolin | 87% |

The active ingredient is mixed and ground with the adjuvants, and the mixture is moistened with water. The mixture is extruded and then dried in a stream of air.

| 2.5. Coated granulate | |
|---|---|
| a compound from the Tables | 3% |
| polyethylene glycol (MW 200) | 3% |
| kaolin | 94% |
| (MW = molecular weight) | |

The finely ground active ingredient is uniformly applied, in a mixer, t the kaolin moistened with polyethylene glycol. Non-dusty coated granulates are obtained in this manner.

| 2.6. Suspension concentrate | |
|---|---|
| a compound from the Tables | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the adjuvants, giving a suspension concentrate from which suspensions of any desired concentration can be obtained by dilution with water.

3. Biological Examples

Example 3.1

Action against Colletotrichum lagenarium on Cucumis sativus L.

(a) After 2 weeks' cultivation, cucumber plants are sprayed with a spray mixture prepared from a wettable powder formulation of the test compound (concentration: 200 ppm).

After 48 hours the plants are infected with a spore suspension ($1.5 \times 10^5$ spores/ml) of the fungus and incubated for 36 hours at high humidity and a temperature of 23° C. Incubation is then continued at normal humidity and at from 22° C. to 23° C.

The protective action is assessed on the basis of the fungal attack 7 to 8 days after infection.

(b) After 2 weeks' cultivation, cucumber plants are treated by soil application with a spray mixture prepared from a wettable powder formulation of the test compound (concentration: 60 or 20 ppm based on the volume of soil).

After 48 hours the plants are infected with a spore suspension ($1.5 \times 10^5$ spores/ml) of the fungus and incubated for 36 hours at high humidity and a temperature of 23° C. Incubation is then continued at normal humidity and at 22° C.

The protective action is assessed on the basis of the fungal attack 7 to 8 days after infection.

(c) After 2 weeks' cultivation, cucumber plants are treated with a spray mixture prepared from a wettable powder formulation of the test compound (concentration: 200 ppm).

After 3 weeks the plants are infected with a spore suspension (1.5×105 spores/ml) of the fungus and incubated for 36 hours at high humidity and a temperature of 23° C. Incubation is then continued at normal humidity and at from 22° to 23° C.

The protective action is assessed on the basis of the fungal attack 7 to 8 days after infection.

Compounds from Tables 1 to 3 exhibited good activity in tests (a) and (b). For example, compounds 1.1, 1.2, 1.6, 1.7, 1.8 and 1.23 confined fungal attack to 0 to 20%. On the other hand, Colletotrichum attack was 100% on untreated and infected control plants.

Example 3.2

Action against Puccinia graminis on wheat (a) Wheat plants are sprayed 6 days after sowing with a spray mixture (0.02% active ingredient) prepared from a wettable powder formulation of the test compound. After 24 hours the treated plants are infected with a uredospore suspension of the fungus. The infected plants are incubated for 48 hours at 95-100% relative humidity and about 20° C. and then stood in a greenhouse at about 22° C. Evaluation of rust pustule development is made 12 days after infection.

(b) 5 days after sowing wheat plants are treated with a spray mixture (0.006% active ingredient based on the volume of soil) prepared from a wettable powder formulation of the test compound. After 48 hours the treated plants are infected with a uredospore suspension of the fungus. The infected plants are incubated for 48 hours at 95-100% relative humidity and about 20° C. and then stood in a greenhouse at about 22° C. Evaluation of rust pustule development is made 12 days after infection.

Compounds from Tables 1 to 3 exhibited good activity against Puccinia fungi. For example, compounds 1.1, 1.2, 1.30, 2.1, 2.2, 2.3 and 3.7 confined fungal attack to 0 to 20%. On the other hand, Puccinia attack was 100% on untreated and infected control plants.

Example 3.3:

Action against Phytophthora infestans on tomato plants (a) After 3 weeks' cultivation, tomato plants are sprayed with a spray mixture (0.02% active ingredient) prepared from a wettable powder formulation of the test compound. After 24 hours the treated plants are infected with a sporangia suspension of the fungus. The fungal attack was evaluated after incubating the infected plants for 5 days at 90-100% relative humidity and 20° C.

(b) After a cultivation period of 3 weeks, tomato plants are watered with a spray mixture (0.006% active ingredient based on the volume of soil) prepared from a wettable powder formulation of the test compound. Care is taken that the spray mixture does not come into contact with the parts of the plants that are above the soil. After 48 hours the treated plants are infected with a sporangia suspension of the fungus. The fungal attack is evaluated after incubating the infected plants for 5 days at 90-100% relative humidity and 20° C.

Compounds from Tables 1 to 3 exhibited a good protective action against the Phytophthora fungus. For example, compounds 1.13, 1.17, 1.20 and 1.32 confined fungal attack to 0 to 20%. On the other hand, Phytophthora attack was 100% on untreated and infected control plants.

Example 3.4

Action against Cercospora arachidicola on groundnut plants

Groundnut plants 10-15 cm in height are sprayed with a spray mixture (0.02% active ingredient) prepared from a wettable powder formulation of the test compound, and infected 48 hours later with a conidia suspension of the fungus. The infected plants are incubated for 72 hours at about 21° C. and high humidity and then stood in a greenhouse until the typical leaf specks appear.

Evaluation of the fungicidal action is effected 12 days after infection based on the number and size of the specks.

Compared with untreated and infected control plants (number and size of the specks =100%), Cercospora attack on groundnut plants that had been treated with compounds from Tables 1 to 3 was reduced.

Example 3.5

Action against Plasmopara viticola on vines (a) Vine seedlings at the 4 to 5 leaf stage are sprayed with a spray mixture (0.02% active ingredient) prepared from a wettable powder formulation of the test compound. After 24 hours the treated plants are infected with a sporangia suspension of the fungus. Fungal attack is evaluated after incubation for 6 days at 95-100% relative humidity and 20° C.

(b) Vine seedlings at the 4 to 5 leaf stage are infected with a sporangia suspension of the fungus. After having been incubated for 24 hours in a humidity chamber at 95-100% relative humidity and 20° C., the infected plants are dried and sprayed with a spray mixture (0.06% active ingredient) prepared from a wettable powder formulation of the test compound. After the spray coating has dried the treated plants are placed in the humidity chamber again. The fungal attack is evaluated 6 days after infection.

Compounds from Tables 1 to 3 exhibited a good protective action against Plasmopara viticola. For example compound 1.8 confined fungal attack to 0-20%. On the other hand, Plasmopara attack was 100% on untreated and infected control plants.

Example 3.6

Action against Pyricularia oryzae on rice plants (a) After 2 weeks' cultivation, rice plants are sprayed with a spray mixture (0.02% active ingredient) prepared from a wettable powder formulation of the test compound. After 48 hours, the treated plants are infected with a conidia suspension of the fungus. Evaluation of fungal attack is made after incubation for 5 days at 95-100% relative humidity and 24° C.

(b) 2 week-old rice plants are watered with a spray mixture (0.006% active ingredient based on the volume of soil) prepared from a wettable powder formulation of the test compound. The pots are then filled with water until the lowest parts of the stalks of the rice plants stand in water. After 96 hours the treated rice plants are infected with a conidia suspension of the fungus. Evaluation of fungal attack is made after incubation of the infected plants for 5 days at 95-100% relative humidity and approximately 24° C.

Rice plants that had been treated with a spray mixture containing one of the compounds from Tables 1 to 3 as active ingredient exhibited only slight fungal attack compared with untreated control plants (100% attack). For example, in test (a), compounds 1.6. 1.8, 1.29 and 1.33 and, in test (b), compounds 1.6 and 1.33 confined fungal attack to 0 to 20%.

Example 3.7

Action against Pseudomonas tomato on tomato plants (a) After 3 weeks' cultivation tomato plants are treated by foliar application with a spray mixture prepared from a wettable powder formulation of the test compound (concentration: 200 ppm). After 3.5 weeks the plants are inoculated with a bacterial suspension ($10^8$ bacteria/ml) and incubated for 6 days at high humidity and at a temperature of 25° C. The protective action is evaluated 7 to 8 days after inoculation on the basis of the bacterial attack.

(b) After 3 weeks' cultivation tomato plants are treated by soil application with a spray mixture prepared from a wettable powder formulation of the test compound (concentration: 60 ppm based on the volume of soil). After 3.5 weeks the plants are inoculated with a bacterial suspension (108 bacteria/ml) and incubated for 6 days at high humidity and at a temperature of 25° C.

The protective action is evaluated 7 to 8 days after inoculation on the basis of the bacterial attack.

Compounds from Tables 1 to 3 exhibited a good protective action against Pseudomonas. For example, in test (a), compounds 1.1, 1.23, 1.30 and 1.32 and, in test (b), compounds 1.1, 1.8, 1.23, 1.24, 1.25, 1.27, 1.28, 1.30, 1.32, 1.34 and 2.1 confined bacterial attack to 0 to 20%. On the other hand, Pseudomonas attack was 100% on untreated and infected control plants.

Example 3.8

Action against Tobacco Mosaic virus on tobacco 8-week-old tobacco plants are sprayed (concentration: 200 ppm) or injected (concentration: 200 ppm) with a formulated solution of the test compound. After 4 days the plants are mechanically inoculated with a suspension of Tobacco Mosaic Virus (0.5 µg/ml+carborundum) and incubated at a temperature of 20°-22° C.

The protective action is evaluated 7 days after inoculation on the basis of the number and size of the local lesions.

Compounds from Tables 1 to 3 exhibited a good protective action against Tobacco Mosaic Virus. Lesions of 100% were, however, observed on untreated and infected control plants.

Example 3.9

Action against Pseudomonas lachrymans on Cucumis sativus L.

(a) After 2 weeks' cultivation, cucumber plants are sprayed with a spray mixture prepared from a wettable powder formulation of the test compound (concentration: 20 ppm).

After 1 week, the plants are infected with a bacterial suspension ($10^8$ bacteria/ml) and incubated for 7 days at high humidity and a temperature of 23° C.

The protective action is evaluated 7 to 8 days after infection on the basis of the bacterial attack.

(b) After 2 weeks' cultivation cucumber plants are treated by soil application with a spray mixture prepared from a wettable powder formulation of the test compound (concentrations: 60, 20, 6, 2 ppm based on the volume of soil).

After 1 week the plants are infected with a bacterial suspension ($10^8$ bacteria/ml) and incubated for 7 days at high humidity and a temperature of 23° C.

The protective action is evaluated 7 to 8 days after infection on the basis of the bacterial attack.

Compounds from Tables 1 to 3 exhibited a good protective action against Pseudomonas attack. For example bacterial attack was confined to 0 to 20% in test (a) by compounds 1.8 and 1.23 and in test (b) by compound 1.23. On the other hand, Pseudomonas attack was 100% on untreated and infected control plants.

Example 3.10

Action against Xanthomonas oryzae on rice (Oryza sativa)

(a) After 3 weeks' cultivation in a greenhouse, rice plants of the variety "Calora" or "S6" are sprayed with the test substance in the form of a spray mixture (0.02% active ingredient). After this spray coating has dried for 1 day the plants are placed in a climatic chamber at 24° C. and 75-85 % relative humidity and infected. The infection is carried out by cutting off the leaf tips with shears that have beforehand been immersed in a suspension of Xanthomonas oryzae. After an incubation period of 10 days the cut leaves that have been attacked become shrivelled, roll up and become necrotic. The residual activity of the test substance is evaluated on the basis of the extent of these disease symptoms.

(b) After a cultivation period of 3 weeks in a greenhouse, rice plants of the variety "Calora" or "S6" are watered with a suspension of the test substance (0.006% active ingredient based on the volume of soil). Three days after this treatment the plants are placed in a climatic chamber at 24° C. and 75-85% relative humidity and infected. The infection is carried out by cutting off the leaf tips with shears that have beforehand been immersed in a suspension of Xanthomonas oryzae. After an incubation period of 10 days the cut leaves that have been attacked become shrivelled, roll up and become necrotic. The systemic activity of the test substance is evaluated on the basis of the extent of these disease symptoms.

Compounds from Tables 1 to 3 exhibited a good protective action against Xanthomonas oryzae. For example, in test (a), compounds 1.1, 1.23 and 1.32 and, in test (b) compounds 1.1, 1.30, 1.31, 1.32, 1.33, 1.34, 1.35, 1.36 and 2.1 confined the bacterial attack to 0 to 20%. On the other hand, disease attack was 100% on untreated and infected control plants.

Example 3.11

Action against Xanthomonas vesicatoria on paprika (Capsicum annuum)

(a) After 3 weeks' cultivation in a greenhouse, paprika plants of the variety "California Wonder" are sprayed with the test substance in the form of a spray mixture (0.02% active ingredient). After the spray coating has dried for one day, the plants are placed in a climatic chamber at 26° C. and 95-100% relative humidity and infected by spraying the underside of the leaves with a standardised suspension of Xanthomonas vesicatoria. After an incubation period of 6 days, round, initially watery, later necrotic, light specks form on the leaves attacked. The residual activity of the test substance is evaluated on the basis of the extent of these flecks.

(b) After a cultivation period of 3 weeks in a greenhouse, paprika plants of the variety "California Wonder" are watered with a suspension of the test substance (0.006% active ingredient based on the volume of soil). Three days after this treatment the plants are placed in a climatic chamber at 26° C. and 95–100% relative humidity and infected by spraying the undersides of the leaves with a standardised suspension of Xanthomonas vesicatoria. After an incubation period of 6 days, round, initially watery, later necrotic, light specks form on the leaves attacked. The systemic activity of the test substance is evaluated on the basis of the extent of these flecks.

Compounds from Tables 1 to 3 exhibited a good protective action against Xanthomonas vesicatoria. For example, in test (a), compound 1.32 and, in test (b), compounds 1.23, 1.30, 1.32, 1.38, 1.39, 2.1, 2.2 and 2.3 confined the bacterial attack to 0 to 20%. On the other hand, disease attack was 100% on untreated and infected control plants.

Example 3.12

Dressing action against Fusarium nivale in rye

Rye seeds of the variety Tetrahell naturally infected with Fusarium nivale are dressed with the test substance on a mixer roll, the following concentrations being used: 600, 200 or 60 ppm a.i. (based on the weight of the seed).

The infected and treated rye is sown in October in the open with a seeder in plots 3 meters long containing 6 rows. Three replicates are carried out with each test compound.

Until the attack is evaluated, the test plants are cultivated under normal field conditions (preferably in a region with unbroken snow cover during the winter months).

To determine the effectiveness of the test compounds, the percentage of plants attacked by Fusarium is assessed in Spring directly after the snow has melted.

Compounds from Tables 1 to 3 exhibited a good protective action against Fusarium. On the other hand, disease attack on untreated and infected control plants was 100%.

Example 3.13

Dressing action against Helminthosporium gramineum on barley

Winter barley seeds of the variety "C1" naturally infected with Helminthosporium gramineum are dressed with the test substance on a mixer roll, the following concentrations being used: 600, 200 or 60 ppm a.i. (based on the weight of the seed).

The infected and treated barley is sown in October in the open with a seeder in plots 2 meters long containing 3 rows. Three replicates are carried out with each test compound.

Until the attack is evaluated, the test plants are cultivated under normal field conditions.

To determine the effectiveness of the test compounds, the percentage of stalks attacked by Helminthosporium is assessed at the time of ear emergence.

Compounds from Tables 1 to 3 exhibited a good protective action against Helminthospora. On the other hand, disease attack was 100% on untreated and infected control plants.

Example 3.14

Dressing action against Ustilago nuda on barley

Winter barley seeds of the variety "RM1" naturally infected with Ustilago nuda are dressed with the test substance on a mixer roll, the following concentrations being used: 600, 200 or 60 ppm a.i. (based on the weight of the seed).

The infected and treated barley is sown in October in the open with a seeder in plots 2 meters long containing 3 rows. Three replicates are carried out with each test compound.

Until the attack is evaluated, the test plants are cultivated under normal field conditions.

To determine the effectiveness of the test compounds, the percentage of ears attacked by Ustilago is assessed when the plants are in bloom.

Compounds from Tables 1 to 3 exhibited a good protective action against Ustilago. On the other hand, disease attack was 100% on untreated and infected control plants.

Example 3.15

Dressing action against Colletotrichum lagenarium on Cucumis sativus L.

Cucumber seeds are dressed with a solution of the active ingredient (concentration: 180 g/100 kg of seed). The seeds are sown. After 4 weeks the plants are infected with a spore suspension ($1.5 \times 10^5$ spores/ml) of the fungus and incubated for 36 hours at high humidity and a temperature of 23° C. The incubation is then continued at normal humidity and at from 22° to 23° C. The protective action is evaluated on the basis of the fungal attack 7 to 8 days after infection.

Compounds from Tables 1 to 3 exhibited a good protective action against Colletotrichum. Fungal attack was 100% on infected control plants, where the seeds had not been treated.

Example 3.16

Residual-protective action against Venturia inaequalis on apple shoots

Apple cuttings with 10–20 cm long fresh shoots are sprayed with a spray mixture (0.02% active ingredient) prepared from a wettable powder formulation of the test compound. The treated plants are infected 24 hours later with a conidia suspension of the fungus. The plants are then incubated for 5 days at 90–100% relative humidity and stood in a greenhouse for a further 10 days at 20°–24° C. Scab attack was evaluated 15 days after infection.

Compounds from Tables 1 to 3 exhibited a good protective action against Venturia. For example compound 1.32 confined scab attack to 5 to 20%. On the other hand, Venturia attack was 100% on untreated and infected shoots.

Example 3.17

Action against Erysiphe graminis on barley (a) Barley plants about 8 cm in height are sprayed with a spray mixture (0.02% active ingredient) prepared from a wettable powder formulation of the test compound. 3 to 4 hours later, the treated plants are dusted with conidia of the fungus. The infected barley plants are stood in a greenhouse at about 22° C. and the fungal attack is evaluated after 10 days.

(b) Barley plants about 8 cm in height are watered with a spray mixture (0.006% active ingredient, based on the volume of soil) prepared from a wettable powder formulation of the test compound. Care is taken that the spray mixture does not come into contact with the parts of the plants above the soil.

The treated plants are dusted 48 hours later with conidia of the fungus. The infected barley plants are stood in a greenhouse at about 22° C. and evaluation of fungal attack is made after 10 days.

Compounds from Tables 1 to 3 exhibited a good protective action against Erysiphe. For example compounds 1.24, 2.2 and 2.3 confined fungal attack to less than 20%, whilst attack on untreated and infected control plants was 100%.

What is claimed:

1. A compound of formula I

[Structure I: pyridine ring with two Hal substituents, bearing —CO—NH—(Y)$_n$—X]

in which
  Hal, each independently of the other, is fluorine, chlorine, bromine or
  Y is CH-R$_1$ or NH;
  n is 1 or 0;
  R$_1$ is hydrogen or C$_1$-C$_4$alkyl;
  X is a heterocycle selected from the group consisting of furan-2-yl, furan-3-yl, thiophen-2-yl, thiophen-3-yl, imidazol-2-yl, 4,5-imidazolin-2-yl, pyrazol-3-pyrazolin-3-yl, 1,2,4-triazol-3-yl, 1,2,4-triazol-4-yl, oxazol-2-yl, isoxazo isoxazol-3-yl, thiazol-2-yl, isothiazol-3-yl, isothiazol-5-yl, 1,3,4-thiadia 3,4-thiadiazol-3-yl, 1,3,4-oxodiazol-3-yl or 1,2,4-oxadizol-3-yl, 3-thiono-1,2-dithia-4-azol-5-yl, 2-thionothiazolin-4-on-3-yl, 1,3,4-oxy-4,5-dihydrooxazol-3-yl, 1,3,4-oxoadiazol-2-yl, 1,2,4-thiadiazol-5-yl and 1,2,4-thiadiazol-3-yl, said heterocycle being unsubstituted or substituted by C$_1$-C$_8$-alkyl, halogen, trifluoromethyl, cyano or nitro.

2. A compound according to claim 1 of formula Ia

[Structure Ia: pyridine ring with two Hal substituents, bearing —CO—NH—CH(R$_1$)—X]

in which
  Hal, each independently of the other, is fluorine, chlorine or bromine;

R$_1$ is hydrogen or C$_1$-C$_4$alkyl; X is a heterocycle as specified for formula I.

3. Compounds according to claim 1 of formula Ib

[Structure Ib: pyridine ring with two Hal substituents, bearing —CO—NH—NH—X]

in which
  Hal, each independently of the other, is fluorine, chlorine or bromine;
  X is a heterocycle as specified for formula I.

4. Compounds according to claim 1 of formula Ic

[Structure Ic: pyridine ring with two Hal substituents, bearing —CO—NH—X]

in which
  Hal, each independently of the other, is fluorine, chlorine or bromine;
  X is a heterocycle as specified for formula I.

5. Compounds according to claim 2 in which:
  Hal is chlorine or bromine;
  R$_1$ is hydrogen;
  X is furan-2-yl, 1,2,4-triazol-3-yl, thiazol-2-yl, thiazol-5-yl, isothiazol-3-yl, oxazol-2-yl, isoxazol-3-yl, isoxazol-5-yl, 1,3,4-thiadiazol-2-yl, 1,2,4-thiadiazol-3-yl or 3-thiono-1,2-dithia-4-azol-5-yl.

6. Compounds according to claim 3 in which:
  Hal is chlorine or bromine;
  X is furan-2-yl, 1,2,4-triazol-3-yl, thiazol-2-yl, thiazol-5-yl, isothiazol-3-yl, oxazol-2-yl, isoxazol-3-yl, isoxazol-5-yl, 1,3,4-thiadiazol-2-yl, 1,2,4-thiadiazol-3-yl or 3-thiono-1,2-dithia-4-azol-5-yl.

7. A compound from the group:
  3-methylisoxazole-5-(2,6-dichloroisonicotinic acid) amide,
  5-methylisoxazole-3-(2,6-dichloroisonicotinic acid) amide,
  α-methylfurfuryl-2,6-dichloroisonicotinic acid amide,
  3-methylisothiazole-5-(2,6-dichloroisonicotinic acid) amide.

8. A composition for protecting plants against attack by microorganisms that contains as active component an effective amount of at least one compound according to claim 1 together with customary carriers and adjuvants.

9. A method of protecting plants against attack by phytopathogenic microorganisms which comprises applying as active ingredient to the plant or the locus thereof a compound according to claim 1.

* * * * *